(12) United States Patent
Critzer et al.

(10) Patent No.: US 7,322,356 B2
(45) Date of Patent: Jan. 29, 2008

(54) COMBINATION SLEEP APNEA TREATMENT (75) Inventors: Susan L. Critzer, Dellwood, MN (US); Timothy R. Conrad, Eden Prairie, MN (US)

(73) Assignee: Restore Medical, Inc., St. Paul, MN (US)

( * ) Notice: Subject to any disclaimer, the term of this patent is extended or adjusted under 35 U.S.C. 154(b) by 370 days.

(21) Appl. No.: 11/064,641

(22) Filed: Feb. 24, 2005

(65) Prior Publication Data
US 2006/0185673 A1 Aug. 24, 2006

(51) Int. Cl.
*A61M 16/00* (2006.01)

(52) U.S. Cl. ............................ 128/204.18; 128/204.23; 128/200.24; 128/848

(58) Field of Classification Search ................ 128/846, 128/848, 863, 205.13, 207.12, 206.11, 207.18, 128/204.18, 204.21, 205.25, 204.23, 200.24; 600/529, 12, 13, 373, 380, 422, 423, 427, 600/534, 26, 42; 607/42, 62, 65, 134, 48
See application file for complete search history.

(56) References Cited

U.S. PATENT DOCUMENTS

| | | | |
|---|---|---|---|
| 4,978,323 A * | 12/1990 | Freedman | .................... 600/12 |
| 5,065,756 A | 11/1991 | Rapoport | |
| 5,146,918 A * | 9/1992 | Kallok et al. | ................... 607/2 |
| 5,148,802 A * | 9/1992 | Sanders et al. | ......... 128/204.18 |
| 5,456,662 A | 10/1995 | Edwards et al. | |
| RE35,339 E | 10/1996 | Rapoport | |
| 5,624,439 A * | 4/1997 | Edwards et al. | .............. 606/45 |
| 5,792,067 A * | 8/1998 | Karell | ......................... 600/534 |
| 6,212,435 B1 * | 4/2001 | Lattner et al. | .............. 607/134 |
| 6,216,702 B1 | 4/2001 | Gjersøe | |
| 6,250,307 B1 | 6/2001 | Conrad et al. | |
| 6,431,174 B1 | 8/2002 | Knudson et al. | |
| 6,513,530 B2 | 2/2003 | Knudson et al. | |
| 6,516,802 B2 * | 2/2003 | Hansen et al. | ......... 128/207.11 |
| 6,523,542 B2 | 2/2003 | Metzger et al. | |
| 6,578,580 B2 | 6/2003 | Conrad et al. | |
| 6,636,767 B1 * | 10/2003 | Knudson et al. | .............. 607/42 |
| 6,752,151 B2 | 6/2004 | Hill | |

(Continued)

FOREIGN PATENT DOCUMENTS

| | | |
|---|---|---|
| DE | 44 12 190 A1 | 10/1995 |
| WO | WO 2005/082452 A1 | 9/2005 |
| WO | WO 2006/072571 A1 | 7/2006 |

OTHER PUBLICATIONS

Ersek et al., "Minimally Invasive Macro Implants," *Worldplast*, vol. I, No. 4, pp. 275-285 (1996).

(Continued)

*Primary Examiner*—Justine R. Yu
*Assistant Examiner*—Shumaya B. Ali
(74) *Attorney, Agent, or Firm*—Merchant & Gould P.C.

(57) ABSTRACT

A method for treating a patient diagnosed with obstructive sleep apnea includes identifying a patient as having sleep apnea susceptible to a first positive airway treatment which is at a first operating pressure level in excess of that which is otherwise tolerable to the patient. The patient is treated with an airway treatment selected to alter a portion of an airway tissue of the patient. The patient is then treated with a second positive airway pressure treatment at a second pressure level, which is below the pressure threshold.

9 Claims, 7 Drawing Sheets

U.S. PATENT DOCUMENTS

| | | | |
|---|---|---|---|
| 6,763,629 B1 | 7/2004 | Bennett | |
| 6,770,022 B2* | 8/2004 | Mechlenburg et al. | 600/9 |
| 6,955,172 B2* | 10/2005 | Nelson et al. | 128/848 |
| 2001/0010010 A1* | 7/2001 | Richmond et al. | 607/42 |
| 2001/0037133 A1* | 11/2001 | Knudson et al. | 607/42 |
| 2004/0139975 A1 | 7/2004 | Nelson et al. | |
| 2004/0149290 A1* | 8/2004 | Nelson et al. | 128/848 |

OTHER PUBLICATIONS

Aboubakr, S. et al., "Long-term facilitation in obstructive sleep apnea patients during NREM slep," *J. Appl. Physiol.*, vol. 91, pp. 2751-2757 (Dec. 2001).

Badr, M., "Effect of ventilatory drive on upper airway patency in humans during NREM sleep," *Respiration Physiology*, vol. 103, No. 1, pp. 1-10 (Jan. 1996).

Boot, H. et al., "Long-Term Results of Uvulopalatopharyngoplasty for Obstructive Sleep Apnea Syndrome," *Laryngoscope*, vol. 110, pp. 469-475 (Mar. 2000).

Boudewyns, A. et al., "Temperature-Controlled Radiofrequency Tissue Volume Reduction of the Soft Palate (Somnoplasty®) in the Treatment of Habitual Snoring: Results of a European Multicenter Trial," *Acta Otolaryngol*, vol. 120, pp. 981-985 (2000).

Brietzke, S. et al., "Injection snoreplasty: How to treat snoring without all the pain and expense," *Otolaryngology-Head and Neck Surgery*, vol. 124, No. 5, pp. 503-510 (May 2001).

Cole, P. et al., "Snoring: A Review and a Reassessment," *The Journal of Otolaryngology*, vol. 24, No. 5, pp. 303-306 (1995).

Coleman, s. et al. "Midline radiofrequency tissue reduction of the palate for bothersome snoring and sleep-disordered breathing: A clinical trial," *Otolaryngology-Head and Neck Surgery*, vol. 122, No. 3, pp. 387-394 (Mar. 2000).

Collard, P. et al., "Why Should We Enlarge the Pharynx in Obstructive Sleep Apnea?," *Sleep*, vol. 19, No. 9, pp. S85-S87 (1996).

Courey, M. et al., "Histologic and Physiologic Effects of Electrocautery, $CO_2$ Laser, and Radiofrequency Injury in the Procine Soft Palate," *Laryngoscope*, vol. 109, pp. 1316-1319 (Aug. 1999).

Dalmasso, F. et al., "Snoring: analysis, measurement, clinical implications and applications," *European Respiratory Journal*, vol. 9, pp. 146-159 (1996).

Dreher, A. et al., "Nasenatmungsbehinderung und schlafbezogene Atmungsstörungen," *Laryngo-Rhino-Otol.*, vol. 78, pp. 313-317 (1999).

Ellis, P. et al., "Surgical relief of snoring due to palatal flutter: a preliminary report," *Annals of the Royal College of Surgeons of England*, vol. 75, pp. 286-290 (1993).

Fischer, Y. et al., "Die Radiofrequenzablation des weichen Gaumens (Somnoplastik)," *HNO*, vol. 48, pp. 33-40 (2000).

Gillette, P. et al., "Pediatric Cardiac Pacing," *Cardiology Clinics*, vol. 10, No. 4, pp. 749-754 (Nov. 1992).

Harries, P. et al., "The surgical treatment of snoring," *The Journal of Laryngology and Otology*, vol. 110, pp. 1105-1106 (Dec. 1996).

Huang, L., "Flutter of Cantilevered Plates in Axial Flow," *Journal of Fluids and Structures*, vol. 9, pp. 127-147 (1995).

Huang, L. et al., "Biomechanics of snoring," *Annals of the Royal College of Surgeons of England*, 5 pages (Jul. 1993).

Hukins, C. et al., "Radiofrequency Tissue Volume Reduction of the Soft Palate in Simple Snoring," *Arch. Otolaryngology Head and Neck Surgery*, vol. 126, pp. 602-606 (May 2000).

Li, K. et al., "Radiofrequency volumetric reduction of the palate: An extended follow-up study," *Otolaryngology-Head and Neck Surgery*, vol. 122, No. 3, pp. 410-414 (Mar. 2000).

LaFrentz, J. et al., "Palatal stiffening techniques for snoring in a novel canine model," *Association for Research in Otolaryngology*, vol. 22, Abstrat 499, pp. 125-126 (1999).

Lemperle, G. et al., "PMMA Microspheres (Artecoll) for Skin and Soft-Tissue Augmentation. Part II: Clinical Investigations," *Plastic and Reconstructive Surgery*, vol. 96, No. 3, pp. 627-634 (Sep. 1995).

Littlefield, P. et al., "Snoring surgery: Which one is best for you?" *ENT-Ear, Nose & Throat Journal*, vol. 78, No. 11, pp. 861-870 (Nov. 1999).

Lorenz, C., "If he Snores—what can you do about it?" *Today's Woman*, 1 page (Jul. 1948).

Mair, E, et al., "Cautery-assisted palatal stiffening operation," *Otolaryngology-Head and Neck Surgery*, vol. 122, No. 4, pp. 547-555 (Apr. 2000).

Parker, J., "An overview of Snoring and Obstructive Sleep Apnea—Part One: Evaluation and Diagnosis," *Northwest Dentistry—Clinical Scientific Feature*, pp. 17-22 (Jan.-Feb. 1995).

Phillips, M., "Stenting therapy for stenosing airway diseases," *Respirology*, vol. 3, No. 4, pp. 215-219 (Dec. 1998).

Schwab, R. et al., "Upper Airway and Soft Tissue Anatomy in Normal Subjects and Patients with Sleep-Disordered Breathing," *Am. J. Respir. Crit. Care Med.*, vol. 152, No. 5, pp. 1673-1689 (1995).

Schwab, R. et al., "Dynamic Upper Airway Imaging during Awake Respiration in Normal Subjects and Patients with Sleep Disordered Breathing," *Am. Rev. Respir. Dis.*, vol. 148, No. 5, pp. 1385-1400 (1993).

Schwab, R. "Upper Airway Imaging," *Clinics in Chest Medicine*, vol. 19, No. 1, pp. 33-54 (Mar. 1998).

Schwartz, R. "Effects of electrical stimulation to the soft palate on snoring and obstructive sleep apnea," *The Journal of Prosthetic Dentistry*, vol. 76, No. 3, pp. 273-281 (Sep. 1996).

Schwartz, A. et al., "Pharyngeal Airway Obstruction in Obstructive Sleep Apnea—Pathophysiology and Clinical Implications," *Otolaryngologic Clinics of North America*, vol. 31, No. 6, pp. 911-918 (Dec. 1998).

Sher, A. et al., "The Efficacy of Surgical Modifications of the Upper Airway in Adults With Obstructive Sleep Apnea Syndrome," *Sleep*, vol. 19, No. 2, pp. 156-177 (1996).

"Our Diagnostic Procedures are a Snap!" *Snap Laboratories, L.L.C.*, 4 pages (Date Unknown).

"Snore-Free Nights—Guaranteed!" *Wellquest International Inc.*, 2 pages (Date Unknown).

"Snoreless™ A Natural Lubricant That Really Works," *Nutrition For Life International*, 2 pages (Dec. 1999).

"Haven't you suffered from Snoring long enough?" *Somnoplasty*$^{sm}$, 2 pages (Date Unknown).

Stauffer, J. et al., "Pharyngeal Size and Resistance in Obstructive Sleep Apnea," *Am. Rev. Respir. Dis.*, vol. 136, pp. 623-627 (1987).

Stuck, B. et al., "Volumetric tissue reduction in radiofrequency surgery of the tongue base," *Otolaryngology-Head and Neck Surgery*, vol. 132, No. 1, pp. 132-135 (Jan. 2005).

Wheatley, J. et al., "Mechanical properties of the upper airway," *Current Opinion in Pulmonary Medicine*, vol. 4, pp. 363-369 (1998).

Wiltfang, J. et al., "First results on daytime submandibular electrostimulation of suprahyoidal muscles to prevent night-time hypopharyngeal collapse in obstructive sleep apnea syndrome," *Int. J. Oral. Maxillofac. Surg.*, vol. 28, pp. 21-25 (1999).

Winter, W. et al., "Enlargement of the lateral pharyngeal fat pad space in pigs increases upper airway resistance," *J. Appl. Physiol.*, vol. 79, No. 3, pp. 726-731 (1995).

Berry, et al., "The Use of Auto-Titrating Continuous Positive Airway Pressure for Treatment of Adult Obstructive Sleep Apnea", *Sleep*, 25 (2) pp. 148-173 (Mar. 2002) (an American Academy of Sleep Medicine review).

Blumen, et al., "Radiofrequency Ablation for the Treatment of Mild to Moderate Obstructive Sleep Apnea", *Laryngoscope 112*, pp. 2086-2092 (Nov. 2002).

Berthon-Jones, et al., "Nasal Continuous Positive Airway Pressure Treatment: Current Realities and Future", *Sleep*, 19 (9) S131-5 (Nov. 1996).

Clark, et al., "A Crossover Study Comparing the Efficacy of Continuous Positive Airway Pressure with Anterior Mandibular Positioning Devices on patients with Obstructive Sleep Apnea", *Chest*, 109 (6) pp. 1477-1483 (Jun. 1996).

"The Pillar® Palatal Implant System: First Results in OSA Patients" by Hein, et al., and presented at the Annual Meeting of the American Academy of Otolaryngology in New York, NY, USA (Sep. 2004).

510k clearance (K040417) from the U.S. Food and Drug Administration indicated for use with the treatment of sleep apnea (Jul. 28, 2004).

510k clearance (K011723) from the U.S. Food and Drug Administration for snoring (Dec. 18, 2002).

Hudgel, et al., "A Long-Term Randomized, Cross-Over Comparison of Auto-Titrating and Standard Nasal Continuous Airway Pressure", *Sleep*, 23 (5) pp. 1-4 (Aug. 2000).

Hukins, "Comparative Study of Autotitrating and Fixed-Pressure CPAP in the Home: A Randomized, Single-Blind Crossover Trial", *Sleep*, 27 (8) pp. 1512-1517 (Dec. 2004).

Hussain, et al., "A Randomized Trial of Auto-Titrating CPAP and Fixed CPAP in the Treatment of Obstructive Sleep Apnea-Hypopnea", *Respiratory Medicine*, 98 pp. 330-333 (Apr. 2004).

Massie, et al., "Comparison Between Automatic and Fixed Positive Airway Pressure Therapy in the Home", *American Journal of Respiratory and Critical Care Medicine*, 167 (1) pp. 20-23 (Jan. 2003).

Mortimore, et al., "Uvulopalatopharyngoplasty May Compromise Nasal CPAP Therapy In Sleep Apnea Syndrome", *Amer. Journal of Respiratory and Critical Care Medicine*, 154 pp. 1759-1762 (Dec. 1996).

Pressman, et al., "Ramp abuse. A Novel Form of Patient Noncompliance to Administration of Nasal Continuous Positive Airway Pressure for Treatment of Obstructive Sleep Apnea", *American Journal of Respiratory and Critical Care Medicine*, 151 (5) pp. 1632-1634 (May 1995).

Seemann et al., "Combination Surgical and Mechanical Therapy for Refractory Cases of Obstructive Sleep Apnea", *Journal of Otolaryngology*, vol. 31, No. 2, pp. 85-88 (2002).

Souter, et al., "Upper Airway Surgery Benefits Patients with Obstructive Sleep Apnoea Who Cannot Tolerate Nasal Continuous Positive Airway Pressure", *Journal of Laryngology and Otology*, 118 (4), pp. 270-274 (Apr. 2004).

\* cited by examiner

COMBINATION SLEEP APNEA TREATMENT

BACKGROUND OF THE INVENTION

1. Field of the Invention

This invention is directed to a method for treating obstructive sleep apnea. More particularly, this invention is directed to a combination treatment for obstructive sleep apnea. Further, this invention is directed toward a combination treatment for obstructive sleep apnea to improve patient compliance with a positive airway pressure treatment.

2. Description of the Prior Art

A. Obstructive Sleep Apnea

Obstructive sleep apnea (OSA) and other sleep disordered breathing conditions have received increased scientific and academic attention. Sleep apnea is characterized by excessive periods of cessation of breathing during sleep. In addition to the inconvenience of daytime sleepiness, obstructive sleep apnea can be associated with significant health consequences including adverse cardiac effects.

OSA patients are generally characterized by degree severity according to a score referred to as an apnea-hypopnea index (AHI) which is a measure of the patient's number of apnea-hypopnea events per hour of sleep. For example, an AHI of 30 represents, on average, 30 such events per hour. While there is no fixed agreement on characterization of the disease severity levels, an AHI less than 10 is generally considered normal. An AHI of 10 to 30 is generally considered mild to moderate. A higher AHI is generally considered severe. Severe OSA patients may experience excessive daytime sleepiness, elevated blood pressure and reduced saturated oxygen levels in the blood.

A patient's AHI is measured during a sleep study in which a sleeping patient's apnea-hypopnea events, saturated oxygen levels and other factors are recorded. Sleep studies (polysomnographies) are performed in a sleep lab where a patient spends the night in the lab with sleep parameters monitored and recorded. Sleep studies may also be performed at home. An example of such is described in U.S. Pat. No. 6,216,702 issued Apr. 17, 2001 (assigned to Camtech AS, Norway).

B. Positive Airway Pressure Treatment

A common treatment for obstructive sleep apnea is positive airway pressure (PAP) treatment. In a PAP treatment, air is delivered under pressure to an OSA patient's airway during sleep. The pressurized airflow maintains patency of the patient's airway preventing airway collapse otherwise associated with OSA. Examples of PAP machinery are shown in U.S. Pat. No. 6,752,151 (assigned to Respironics, Inc., Murrysville, Pa.); U.S. Pat. No. 6,516,802 (assigned to Mallinckrodt, Inc., St. Louis, Mo.) and U.S. Pat. No. 6,763,629 jointly assigned to New York University, New York, N.Y. and Puritan-Bennett Corp., Pleasanton, Calif.).

A PAP treatment may take any one of a number of different forms. Most commonly, the PAP is a continuous positive airway pressure treatment (CPAP) (sometimes referred to as fixed continuous airway pressure). In this treatment, the patient wears a mask covering the nose and mouth. Air is supplied under constant pressure to the mask.

The necessary pressure of the airflow for an effective PAP treatment varies from patient to patient. The setting of the pressure (referred to as "titration") is normally set during a sleep study to find the appropriate pressure for the particular patient to maintain patency.

When used in accordance with a physician's instructions, CPAP can be a very effective treatment for obstructive sleep apnea. However, patient compliance with a CPAP treatment can very low. In addition to not using a CPAP machine on certain nights, the patient may not use the machine for the whole night.

Low CPAP compliance can be attributed to many factors. The mask can be uncomfortable, the noise of the pressurization machine associated with the mask can be disruptive to sleep and the pressurization itself can result in unpleasant side effects such as nasal or throat dryness. Further, bed partner intolerance poses a problem for compliance with a CPAP therapy. A bed partner may complain about the noise of the CPAP machine. Placing a CPAP machine further from the bedside may reduce this disturbance. However, this results in a longer tubing and increased pressure drop in the CPAP machine which can reduce the effectiveness of the CPAP machine.

C. Non-PAP Treatments for OSA i. Appliances and Invasive Surgery

Historically, other treatments for OSA include oral appliances and surgery. Surgical treatments include uvulopalatopharyngoplasty (UPPP) in which the trailing edge of the patient's soft palate is trimmed (e.g., by about 1 cm). These procedures have varying success rates.

Oral appliances also require patient compliance. In at least one study of a removable appliance, the appliance was found to be less effective than CPAP (especially in severe OSA patients) even though it was not as bothersome to patients. Clark, et al., "A Crossover Study Comparing the Efficacy of Continuous Positive Airway Pressure with Anterior Mandibular Positioning Devices on Patients with Obstructive Sleep Apnea", *Chest*, 109 (6) pp. 1477-83 (June 1996).

Historical surgical options such as UPPP are invasive and painful. Further, if not successful, a UPPP may compromise a patient's ability to benefit from a CPAP treatment. Mortimore, et al., "Uvulopalatopharyngoplasty May Compromise Nasal CPAP Therapy In Sleep Apnea Syndrome", *Amer. Journal of Respiratory and Critical Care Medicine*, 154 (6 Pt 1) pp. 1759-62 (December 1996). In Mortimore et al., patients with a prior UPPP could tolerate only a much lower CPAP pressure than non-UPPP patients. However, Seemann et al., "Combination Surgical and Mechanical Therapy for Refractory Cases of Obstructive Sleep Apnea", *Journal of Otolaryngology*, Vol. 31, No. 2, pp. 85-88 (2002), report an average decrease of 4.8 cm $H_2O$ CPAP titration pressure after laser-assisted uvulopalatoplasty (LAUP) (one of the five reported patients experienced a CPAP pressure decrease of 11 cm $H_2O$). A LAUP procedure is less aggressive than a UPPP and scars the exterior surface of the mucosa. This scarring can stiffen the palate but is painful.

ii. Less Invasive Surgery (RF Ablation and Palatal Implants)

Recently, less invasive surgical treatments have been suggested for treatment of obstructive sleep apnea. For example, in Blumen, et al., "Radiofrequency Ablation for the Treatment of Mild to Moderate Obstructive Sleep Apnea", *Laryngoscope*, pp. 2086-2092 (2002), the authors suggest using radio-frequency ablation of the soft palate as an effective treatment for obstructive sleep apnea patients. The radio-frequency ablation of the soft palate is described in U.S. Pat. No. 5,456,662 issued Oct. 10, 1995 (describing radiofrequency ablation of the soft palate to treat snoring).

The United States Food and Drug Administration (FDA) has issued 510(k) clearance No. K040417 for the treatment of mild to moderate obstructive sleep apnea to Restore Medical Inc., St. Paul, Minn., USA (assignee of the present application) for the use of its Pillar® palatal implant treatment. The Pillar® implant is an implant placed in the soft palate to stiffen the soft palate through fibrotic response of palatal tissue to the implant material. The Pillar® implant is described in assignee's related U.S. Pat. No. 6,513,530 issued Feb. 4, 2003.

The efficacy of the Pillar® implant in the treatment of obstructive sleep apnea is reported in a poster entitled "Efficacy of the Pillar® Palatal Implant System: First Results in OSA Patients" by Hein, et al., and presented at the Annual Meeting of the American Academy of Otolaryngologist in New York, N.Y., USA (September 2004). For patients with mild to moderate OSA (i.e., patients having an AHI of 10 to 30 episodes per hour), the Hein, et al., poster reports a mean decrease in AHI of 53.4% as well as a reduction in daytime sleepiness and snoring intensity for those patients reporting an AHI decrease. Of 16 treated patients, 13 experienced an AHI decrease.

A palatal implant such as the Pillar® implant for treating obstructive sleep apnea has many advantages over PAP treatment. A Pillar® implant is placed in the soft palate in a single procedure (commonly three implants are placed in the soft palate during one office visit to an otolarnygologist). After a short recovery period (usually a matter of a few days in which the patient is treated only with a mild pain reliever such as aspirin or the like), the patient has no lasting discomfort from the implant or its placement procedure and no further therapy is needed. This has clear advantages over a CPAP procedure in which the patient must, every night, wear the CPAP device and comply with the CPAP therapy.

iii. Severe OSA Patients and Modifications to PAP to Improve Compliance

Not withstanding its significant advantages, a palatal implant for the treatment of obstructive sleep apnea may not be suitable for all OSA patients. Currently, the Pillar® procedure is only cleared for market release by the FDA for patients who suffer from mild to moderate obstructive sleep apnea.

For patients with severe OSA, CPAP remains the preferred treatment. Unfortunately, CPAP suffers from low patient compliance.

Also, for many OSA patients, the CPAP must be set at a high operating pressure in order to be effective. According to some investigators, the high operating pressure increases a likelihood of low compliance. For patients who cannot tolerate CPAP, historical invasive surgeries remain a painful option. Souter, et al., "Upper Airway Surgery Benefits Patients with Obstructive Sleep Apnoea Who Cannot Tolerate Nasal Continuous Positive Airway Pressure", *Journal of Laryngology and Otology*, 118 (4), pp. 270-4 (April 2004).

Advances have been made in PAP treatments. These include delivery of the pressured air nasally (nCPAP) or through an oral appliance in efforts to increase comfort and compliance. Nasal CPAP still suffers from low compliance. Berthon-Jones, et al., "Nasal Continuous Positive Airway Pressure Treatment: Current Realities and Future", *Sleep*, 19 (9 Suppl) S131-5 (November 1996) report nCPAP as an effective treatment but with a patient dropout rate of 30% and a usage of less than 5 hours per night.

One paper reports on efforts to improve compliance with nCPAP by setting the treatment pressure at an initial low pressure (3 cm H20) and ramping the pressure up over 45 minutes to permit the patient to fall asleep before the higher and more uncomfortable prescribed pressure is administered. However, that paper reports a severely limited effective therapy. Pressman, et al., "Ramp abuse. A Novel Form of Patient Noncompliance to Administration of Nasal Continuous Positive Airway Pressure for Treatment of Obstructive Sleep Apnea", *American Journal of Respiratory and Critical Care Medicine*, 151 (5) pp. 1632-4 (May 1995). Pressman, et al., report a compliance rate for nCPAP varying between 46% to 89%.

Advances also include auto-titrating positive airway pressure (APAP) machines. Frequently, these advances are costly alternatives to traditional CPAP and have there own clinical issues.

Unlike CPAP machines having a constant pressure setting, the APAP machine may vary the pressure over the night in response to timing or sensed parameters. APAP has been used in nCPAP. See, Berthon-Jones, et al., article, supra, where the auto-titration is believed to reduce the mean delivery pressure thereby reducing side effects and increasing patient compliance.

Some authors claim that auto-titration supports a conclusion that a lower operating pressure leads to improved compliance. Hudgel, et al., "A Long-Term Randomized, Cross-Over Comparison of Auto-Titrating and Standard Nasal Continuous Airway Pressure", *Sleep*, 23 (5) pp. 645-8 (August 2000). Hudgel, et al., report APAP had a lower average pressure than CPAP (6.4 v. 10.6 cm $H_2O$) and APAP had a greater average daily machine use (6.0 v. 5.5 hours). See, also, Massie, et al., "Comparison Between Automatic and Fixed Positive Airway Pressure Therapy in the Home", *American Journal of Respiratory and Critical Care Medicine*, 167 (1) pp. 20-3 (January 2003). Massie, et al., suggest patients who require higher fixed CPAP pressures use auto-titrating CPAP more and report greater benefit from this therapy.

Other authors report comparable overall compliance between APAP and CPAP. Hukins, et al., "Comparative Study of Autotitrating and Fixed-Pressure CPAP in the Home: A Randomized, Single-Blind Crossover Trial", *Sleep*, 27 (8) pp. 1512-7 (December 2004). Hukins, et al., report higher compliance with APAP for those patients who reported side effects. Also, the authors reported APAP had lower pressures resulting in lower pressure leaks and fewer reported side effects.

To date, comparative studies of APAP and CPAP have not been conclusive. For example, one study claims APAP is not associated with fewer side effects, better compliance or better satisfaction. Hussain, et al., "A Randomized Trial of Auto-Titrating CPAP and Fixed CPAP in the Treatment of Obstructive Sleep Apnea-Hypopnea", *Respiratory Medicine*, 98 (4) pp. 330-3 (April 2004). Differences may be due to different APAP technologies used in different studies. Berry, et al., "The Use of Auto-Titrating Continuous Positive Airway Pressure for Treatment of Adult Obstructive Sleep Apnea", *Sleep*, 25 (2) pp. 148-73 (March 2002) (an American Academy of Sleep Medicine review).

Therapeutically effective operating pressures for a PAP vary from patient to patient. As the pressure rises, a patient's ability to tolerate the CPAP treatment is reduced. For example, patients frequently have difficulty tolerating a CPAP titrated above a pressure of about 11 cm $H_2O$. At such pressures, compliance is estimated at about 30%. For low pressures (about 4 cm $H_2O$), compliance is estimated to be much higher (about 90%). At higher pressures (e.g., about 20 cm $H_2O$), compliance rates are estimated to be as low as 10%. It will be appreciated these estimates are aggregates for the patient population. An individual's pressure threshold leading to low compliance will vary from patient to patient. A higher compliance rate at a lower pressure setting is probably due to the reduction of pressure related side effects such as nasal or throat dryness. Also, patients may have difficulty exhaling against a fixed pressure.

It is an object of the present invention to coordinate a tissue stiffening procedure with a positive airway pressure treatment to better treat patients with severe obstructive sleep apnea.

SUMMARY OF THE INVENTION

According to a preferred embodiment of the present invention, a method is provided for treating a patient diagnosed with obstructive sleep apnea. The method includes identifying a patient as having sleep apnea susceptible to a first positive airway treatment which is at a first operating pressure level in excess of that which is otherwise tolerable to the patient. The patient is treated with an airway treatment selected to alter a portion of an airway tissue of the patient. The patient is then treated with a second positive airway pressure treatment at a second pressure level, which is below the pressure threshold.

DESCRIPTION OF THE PREFERRED EMBODIMENT

With reference now to the various drawing Figures, in which identical elements are numbered identically throughout, a detailed description of a preferred embodiment of the present invention will now be provided. The teachings of the following U.S. patents are incorporated herein by reference: U.S. Pat. No. 6,250,307 to Conrad et al. dated Jun. 26, 2001; U.S. Pat. No. 6,578,580 to Conrad et al. dated Jun. 17, 2003; U.S. Pat. No. 6,523,542 to Metzger et al. dated Feb. 25, 2003; U.S. Pat. No. 6,513,530 to Knudson et al. dated Feb. 4, 2003; and U.S. Pat. No. 6,431,174 to Knudson et al. dated Aug. 13, 2002.

A. Physiology Background

Figure 1:
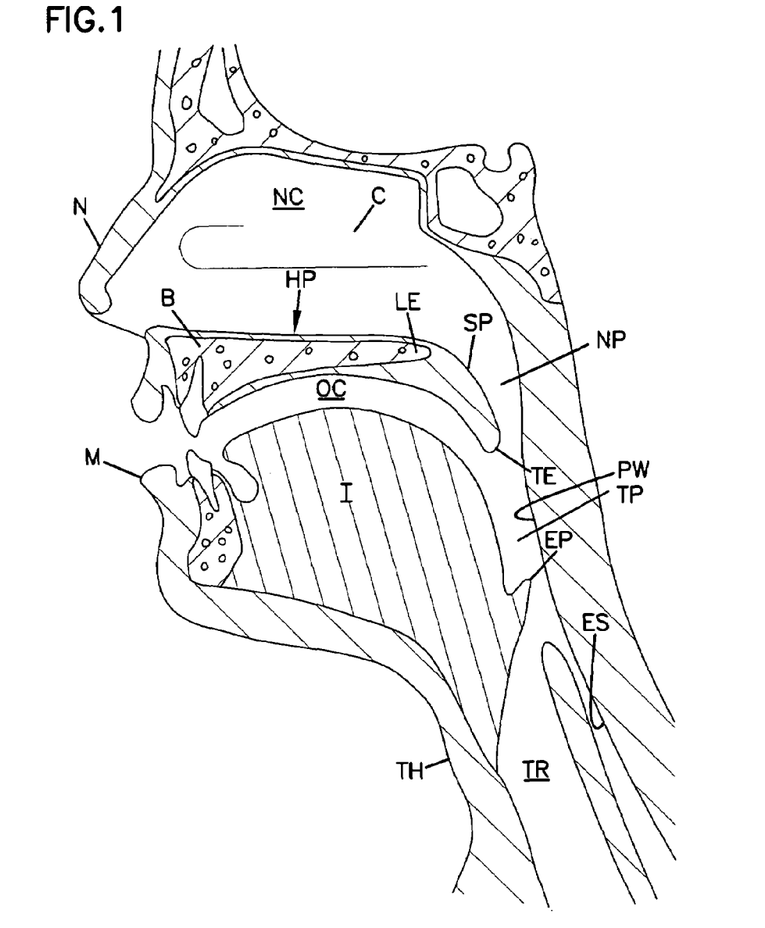
FIG. 1 shows, in cross-section, a naso-pharyngeal area of an untreated patient.
Figure 2:
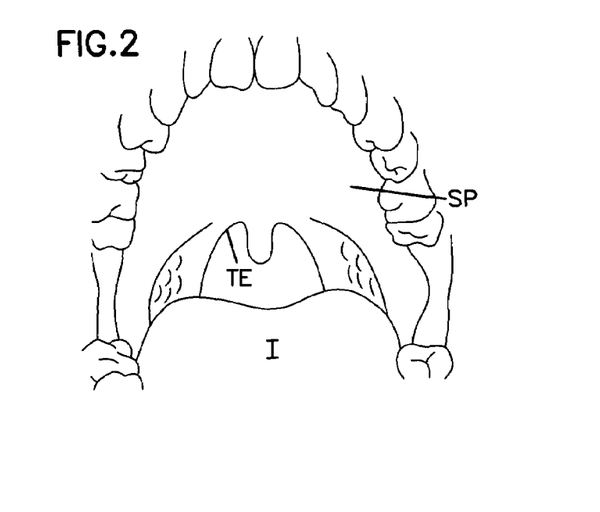
FIG. 2 shows a soft palate viewed through an open mouth of the untreated patient of FIG. 1.

FIG. 1 shows, in cross-section, a naso-pharyngeal area of an untreated patient. FIG. 2 shows a soft palate SP viewed through an open mouth of the untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area (or airway) of the patient with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Snoring and OSA can result from vibration or collapse of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds and OSA. It is not uncommon for vibratory action or collapse from more than one region of the naso-pharyngeal area to contribute to snoring sounds and OSA. Sleep apnea can result from partial or full collapse of the naso-pharyngeal wall during sleep as well as having nasal and palatal contributions.

As indicated above, most of the present discussion will describe placing a stiffening implant in the soft palate SP, it will be appreciated the present invention is applicable to other regions of the naso-pharyngeal area including the nasal concha C and the pharyngeal wall PW.

The snoring sound is generated by impulses caused by rapid obstruction and opening of airways. Huang, et al., state the airway passage opening and closing occurs 50 times per second during a snore. Huang, et al., utilize a spring-mass model (FIG. 5) to illustrate oscillation of the soft palate in response to airflow (where the soft palate is the ball B of mass depending by a spring S from a fixed anchor A).

Figure 3:
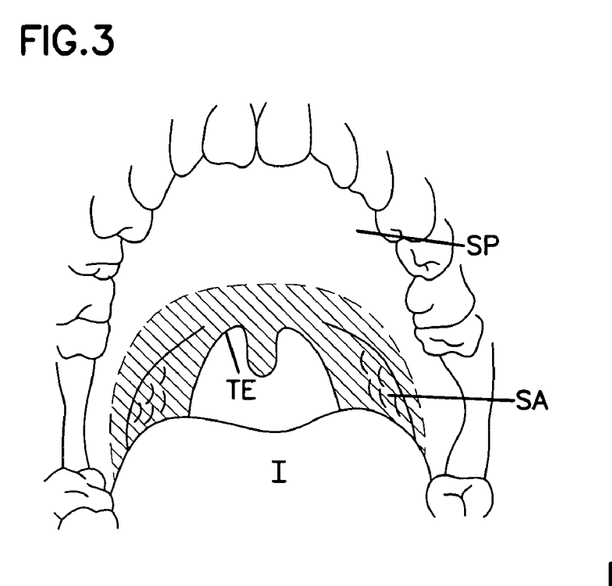
FIG. 3 is a front view of an interior of the mouth shown in FIG. 1 and showing an area to be ablated according to a first prior art surgical procedure.
Figure 4:
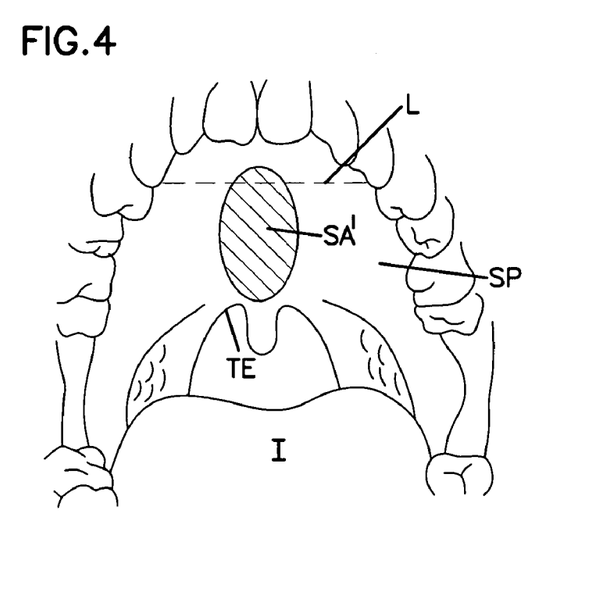
FIG. 4 is the view of FIG. 3 and showing an area to be scarred according to a second prior art surgical procedure.

A prior art technique for treating the soft palate is uvulopalatopharyngoplasty (UPPP). In UPPP, a trailing edge of the soft palate is removed. The shaded area SA in FIG. 3 shows the area of the trailing end TE of the soft palate SP to be removed during this procedure. Huang, et al., analogize the shortening of the soft palate SP in UPPP as effectively raising the critical airflow speed at which soft palate flutter will occur. An alternative procedure proposed by Huang, et al., reduces the flexibility of the soft palate SP through surface scarring which is asserted as affecting the critical flow speed. The shaded area SA' in FIG. 4 shows the area to be scarred by this alternate procedure. In FIG. 4, dashed line L shows the demarcation between the soft and hard palates.

Figure 5:
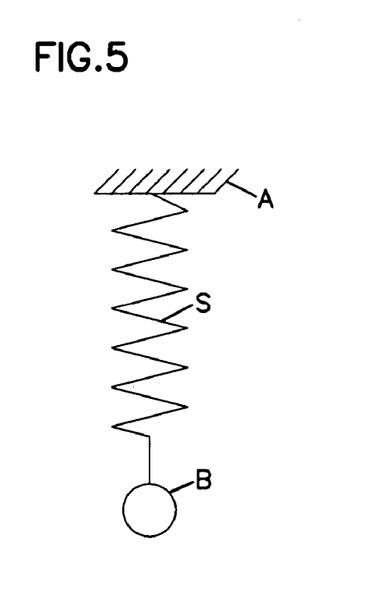
FIG. 5 is a schematic representation of a spring-mass system model of the soft palate.

Using the spring-mass model of FIG. 5 as a convenient model of the soft palate SP, the present invention is directed to a delivery system for a surgical implant for the soft palate SP to alter the elements of the model and thereby alter the dynamic response of the soft palate SP to airflow.

B. Palatal Implants

The present invention is directed to a combination of a tissue stiffening procedure in combination with a positive airway pressure treatment (PAP). The invention will be described with reference to a tissue stiffening procedure involving an implant in the soft palate. While such a stiffening procedure is preferred, others can be used. These include radio-frequency ablation of the soft tissue, sclerosing therapy of the soft palate and collagen injections into the soft palate.

The aforementioned commonly assigned US patents (which have been incorporated herein by reference) describe a wide variety of airway implants for treating snoring or OSA. These patents are U.S. Pat. Nos. 6,250,307; 6,578,580; 6,523,542; 6,513,530 and 6,431,174.

Figure 6:
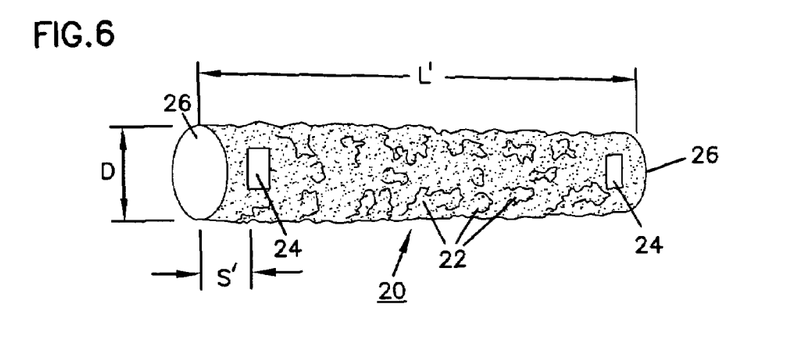
FIG. 6 is perspective view of an implant for use with the present invention.

In a presently preferred embodiment, the implant 20 is a braid of fibers 22. While a single type fiber could be used in implant 20, the implant can be formed of two or more different fibers braided or twisted together. For example, one fiber may be provided for encouraging fibrotic response. Such a fiber may be polyester or silk suture material. The other fiber may be a bio-resorbable fiber (e.g., bio-resorbable suture material which may include natural materials such as collagen or synthetic materials such as the PDS suture material). Alternatively, the other fiber may be a non-resorbable material such as polypropylene suture material to provide added stiffness to the implant.

In a preferred embodiment (shown in FIG. 6), the implant 20 is a composite braid of both air-textured and non-air-textured yarns of polyester formed in a braid of about 2 mm in diameter (D) and 18 mm in length (L'). Welds 24 are formed near the ends 26 of the implant 20 to bond the fibers 22. The welds 24 are spaced from the ends 26 by a spacing S' so that the fibers 22 in the spacing are free to fray and present a fluffier area for tissue in-growth. The implant 20 is fibrosis inducing to induce a fibrotic response of tissue following implantation. An implant having the foregoing characteristics is more fully described in the aforementioned U.S. Pat. No. 6,513,530.

C. Implant Delivery Tool

Figures 7, 8:
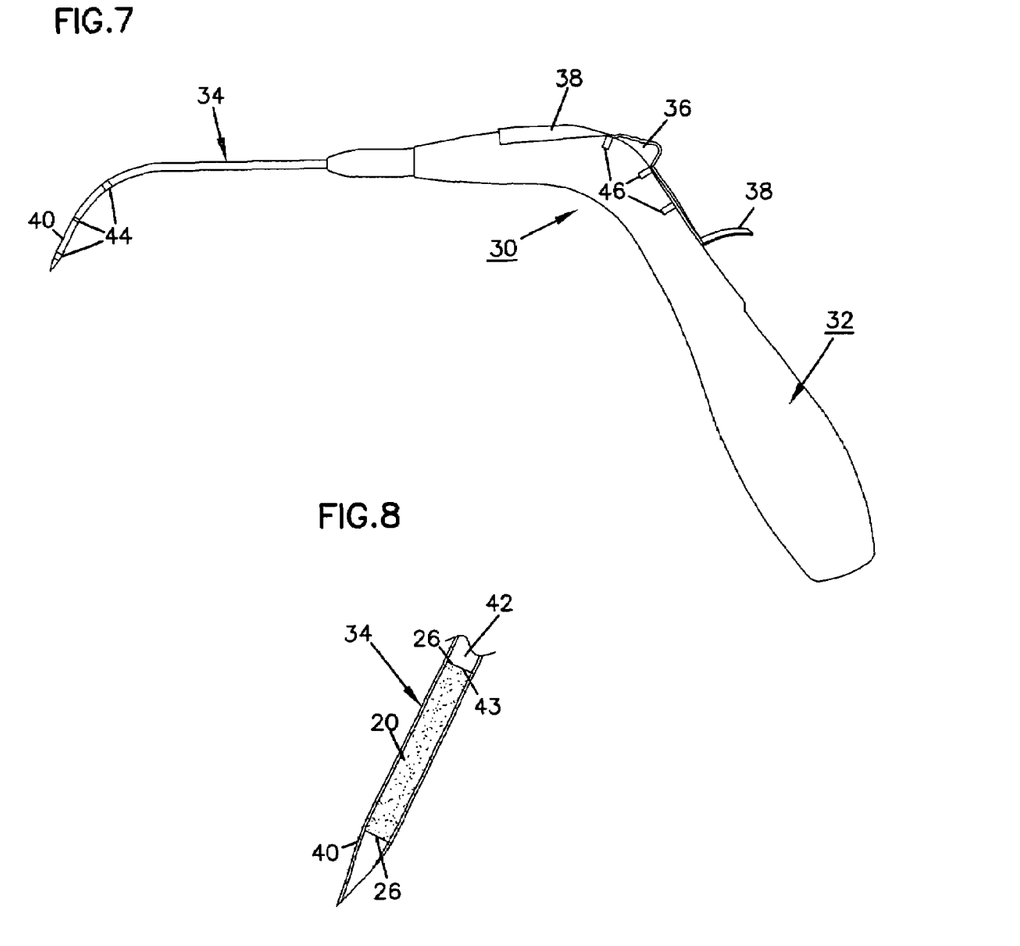
FIG. 7 is a side elevation view of a prior delivery tool for delivery of the implant of FIG. 6 into the soft palate of a patient.
FIG. 8 is a side-sectional view of a distal tip of the tool of FIG. 7 cut-away to reveal the implant of FIG. 6 pre-loaded into the distal tip of the tool.
Figure 9:
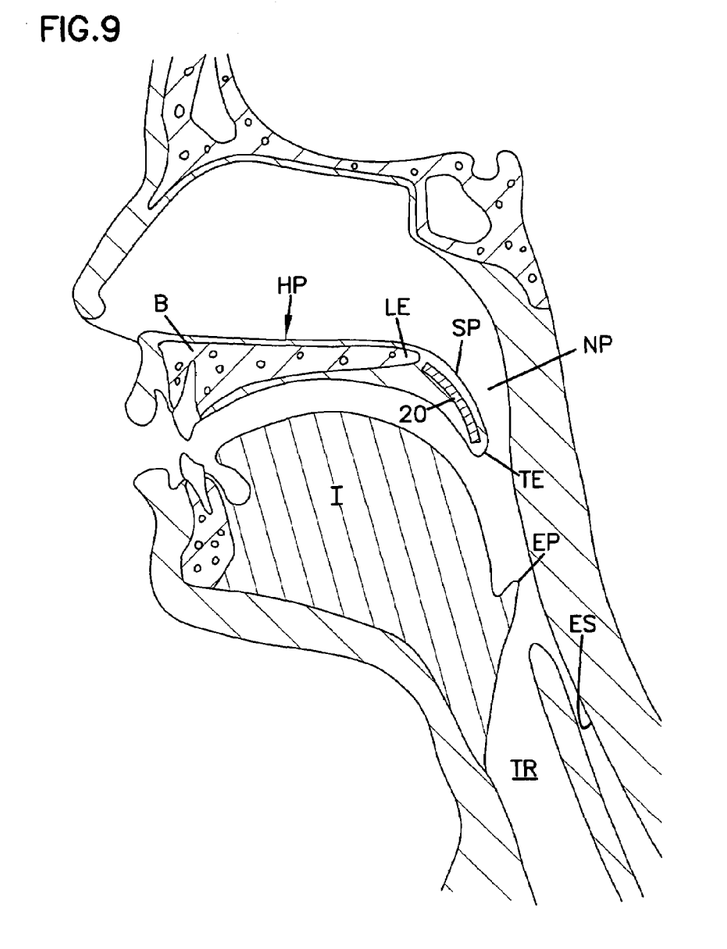
FIG. 9 is the view of FIG. 1 with the soft palate containing the implant of FIG. 6.
Figure 10:
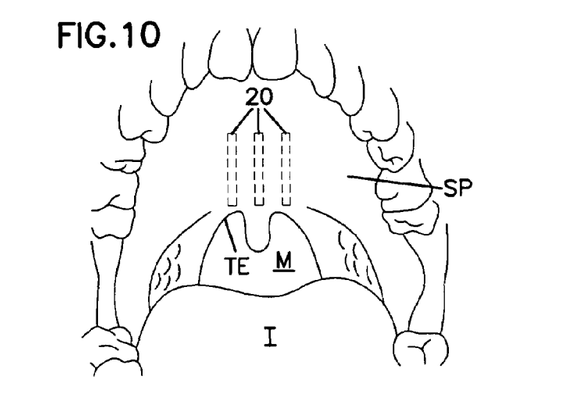
FIG. 10 is the view of FIG. 2 showing three implants of the type of FIG. 6 in the soft palate.

FIGS. 7 and 8 show a prior delivery tool 30 for placing the implant 20 in the soft palate SP. FIGS. 9 and 10 illustrate the desired placement of the implant 20 in the soft palate SP. As shown in FIG. 10, three implants are preferably placed in the soft palate SP. One at the soft palate midline and one each on opposite sides of the midline about 2 mm from the midline.

The delivery tool 30 includes a handle 32 and a needle 34 permanently secured to the handle 32. The handle 32 is designed to be hand-grasped in a pistol-grip manner with a sliding thumb switch 36 positioned to oppose the operator's thumb (not shown) when the handle 32 is grasped. A removable tape 38 covers the thumb switch 36 during shipping and storage to prevent undesired movement of the thumb switch 36. The distal tip 40 of the needle 34 is bent to permit ease of placement of the tip 40 in the soft palate SP without interference of the tool 30 with the patient's teeth or hard palate.

The needle 34 is connected to the thumb switch 36 through linkage (not shown) contained within the handle 32 such that the needle retracts to the right (i.e., moves rearward into the handle 32) as the thumb switch is slid downwardly on the handle 32. Directions "right", "rearward" and "down" are with reference to the orientation shown in FIG. 7.

The distal tip 40 of needle 34 has a bevel ground for piercing tissue of the soft palate. The needle 34 is hollow and carries the implant 20 in sliding close tolerance at the distal tip 40.

An obturator or rod 42 is positioned in the needle 34 between the implant 20 and the handle 32. The obturator 42 is secured to the handle 32 so that is does not retract as the needle retracts. Therefore, as the needle 34 retracts, the needle 34 slides over the fixed-place obturator 42. The distal end 43 of the obturator 42 butts against the implant 20. This prevents the implant 20 from moving with the needle 34 as the needle 34 retracts. As a result, the retracting needle 34 exposes the implant 20.

The implant 20 is carried by the needle 34 to a desired implant site within the soft palate SP. At the desired site, the implant 20 is deployed by retracting the needle 34. Retraction is performed by retracting back on thumb switch 36. Retraction of the needle relative to the handle causes the obturator 42 to dispel the implant 20 from the needle 34. The aforementioned U.S. Pat. No. 6,578,580 describes a retracting needle and stationary rod to deploy an implant in the soft palate. That patent also describes a pre-loaded implant.

The needle has markings 44 to provide indication to an operator of depth of penetration of the needle tip 40 in tissue and location of the implant 20. Corresponding markings 46 are placed on the handle 32 to illustrate the degree of needle retraction and implant exposure relative to sliding movement of the thumb switch 36.

The implant 20 is pre-loaded into the needle 34. The needle 34 is non-removably secured to the handle 32 and all components are delivered in a sterile package. Such packaged implant and its delivery system are the subject of 510k clearance (K011723) from the U.S. Food and Drug Administration for snoring and CE Mark certification (CE 66447) from BSI Product Services indicated for use with the treatment of socially disruptive snoring and obstructive sleep apnea, and 510k clearance (K040417) from the U.S. Food and Drug Administration indicated for use with the treatment of sleep apnea. The product is sold by Restore Medical Inc., St. Paul, Minn., USA—assignee of the present application.

D. Positive Airway Pressure

The present invention is directed to a combination of a tissue stiffening procedure in combination with a positive airway pressure treatment (PAP). The invention will be described with reference to a continuous positive airway pressure (CPAP) treatment. It will be appreciated other treatments such as auto-titrating systems, nasal air delivery systems and oral appliance airway delivery systems could be used. The tissue stiffening procedure is a minimally invasive procedure which stiffens tissue internally (e.g., internal scarring of tissue or stiffening implants placed submucosally within tissue and others as will be described).

Figure 11:
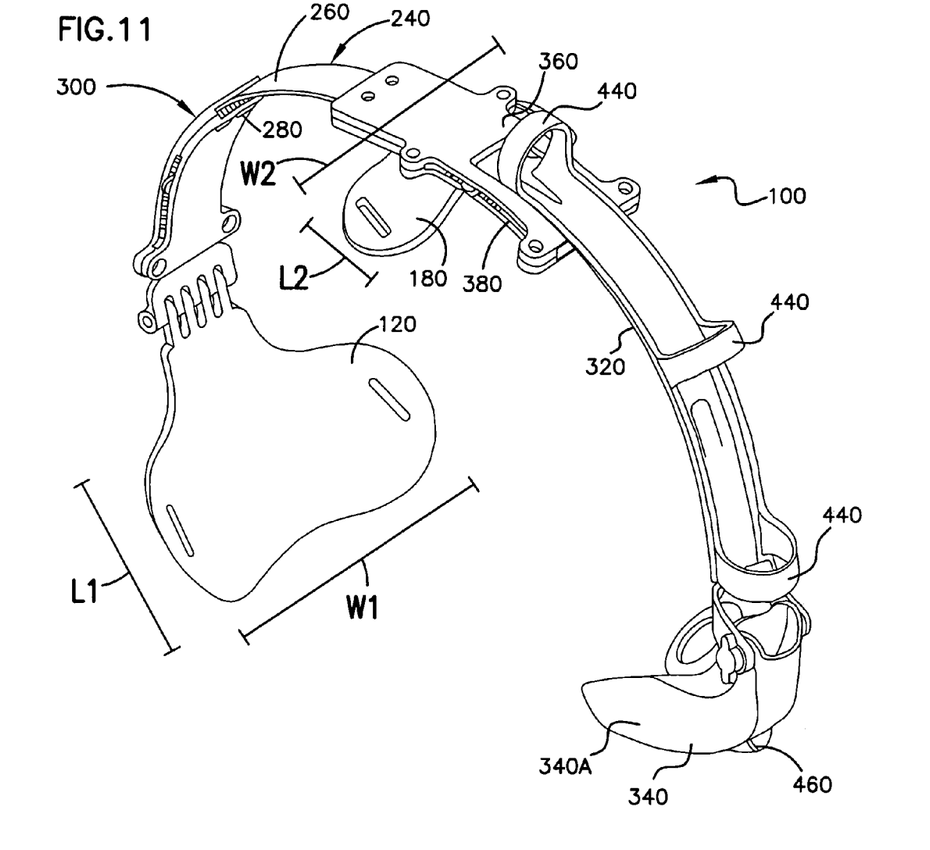
FIG. 11 is a perspective view of a continuous positive airway device (CPAP)

FIG. 11 illustrates a continuous positive airway pressure (CPAP) system such as that shown and described in U.S. Pat. No. 6,516,802 issued Feb. 11, 2003 and assigned to Mallinckrodt, Inc., St. Louis, Mo., USA. The '802 patent is incorporated herein by reference. While the '802 patent disclosure is described herein as a representative example of a CPAP system other CPAP systems may be used which provide airflow to a patient's airway through a mask or other means (e.g., nasal or oral appliance delivery) to treat OSA.

Figure 13:
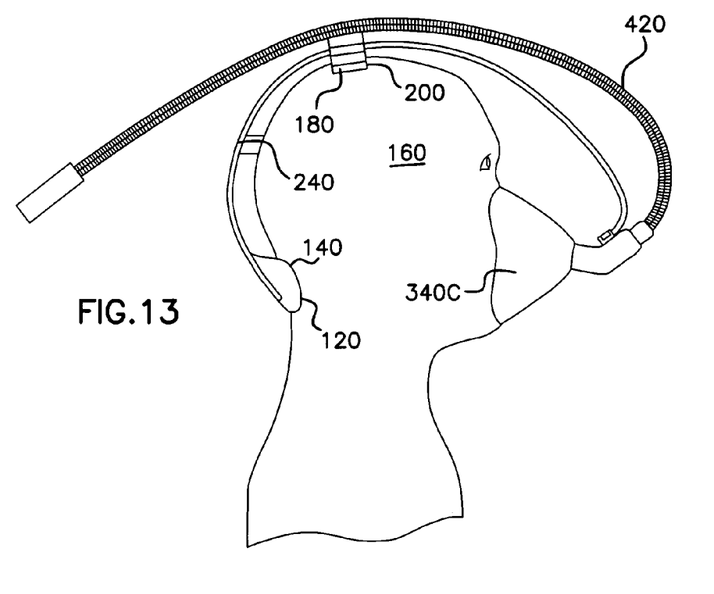
FIG. 13 is a side elevation view of an alternative CPAP device.
Figure 14:
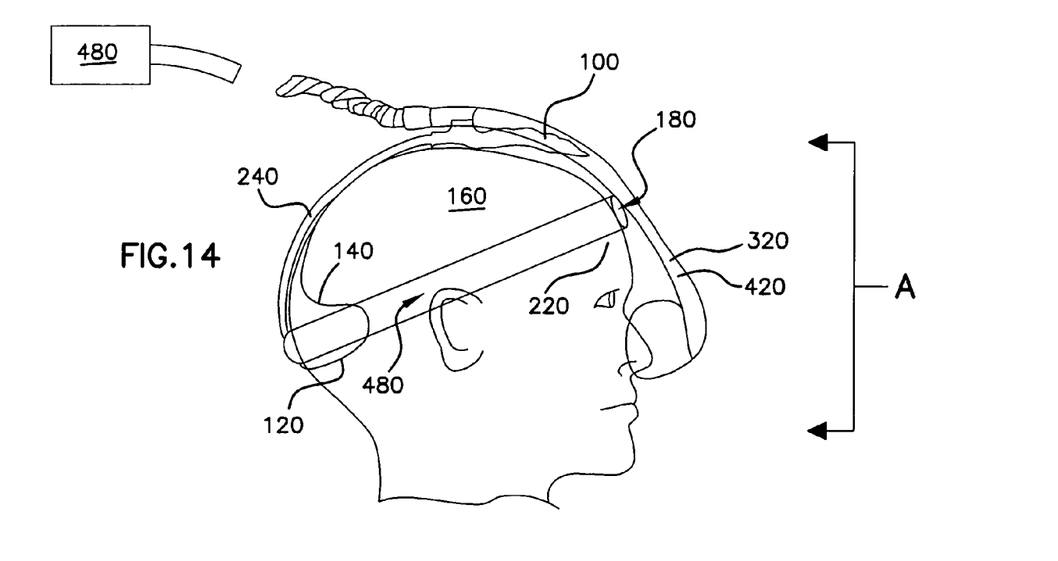
FIG. 14 is a schematic side view of still another embodiment of an alternative CPAP device.
Figure 15:
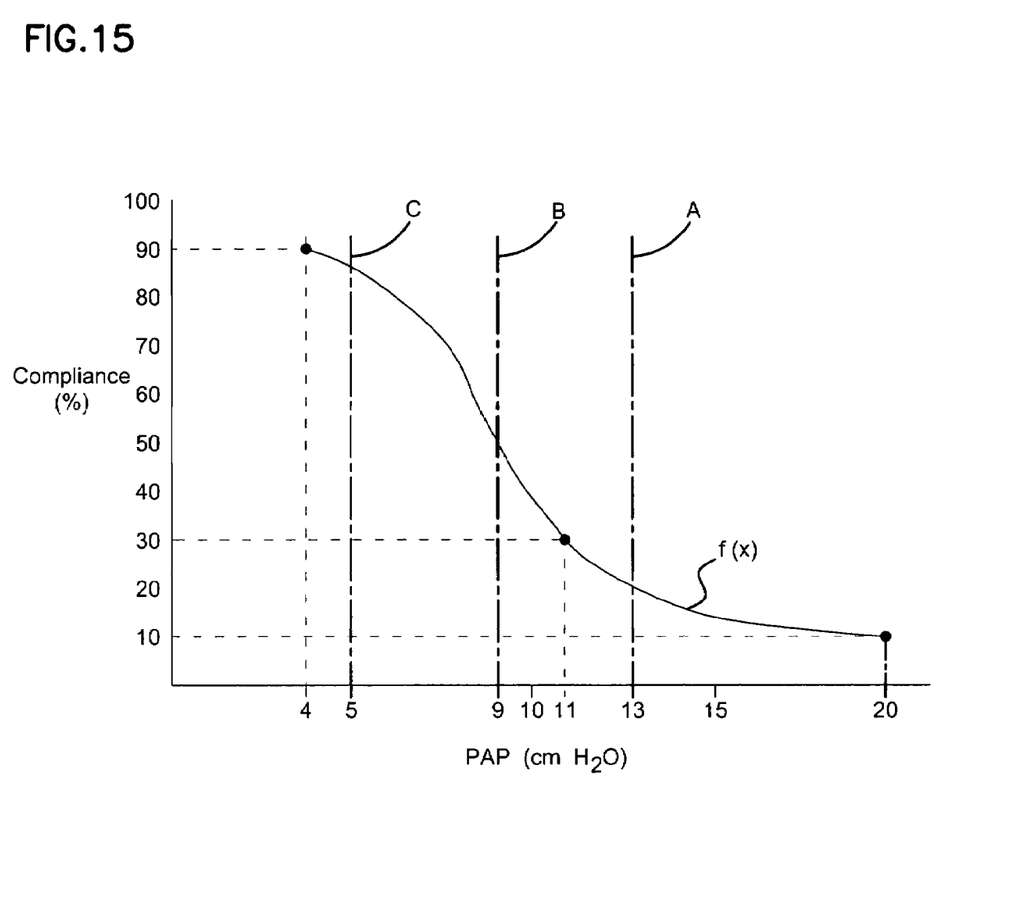
FIG. 15 is a graph illustrating patient compliance with a positive airway pressure (PAP) therapy as a function of the PAP operating pressure for a patient population.

In FIG. 11, a CPAP device 100 includes an occipital anchor 120 for anchoring against the person's head beneath the occipital lobe 140 of a person's head 160 shown in FIGS. 13 and 14. The occipital anchor 120 can have a length L1 within a range of about 2-8 centimeters, preferably about 3-7 centimeters, and a width W1 within a range of about 5 to 20 centimeters, preferably about 8-12 centimeters.

Referring back to FIG. 11, the device 100 includes a forward anchor member 180 for anchoring against a corresponding portion of the person's head selected from the group consisting of a top portion of the person's head 200 shown in FIG. 13, and a forehead portion 220 of a person's head shown in FIG. 14. As shown in FIG. 11, the forward anchor 180 can have a length L2 within a range of about 1 to 4 centimeters, preferably about 2 to 3 centimeters, and a width W2 within a range of about 5 to 11 centimeters, preferably about 7 to 9 centimeters.

The device 100 includes a biasing structure 240 connecting the forward anchor member 180 and the occipital anchor 120. The biasing structure 240 biases the occipital anchor against the occipital lobe and the forward anchor against the top portion or the forehead portion of the person's head, so as to attach the device to the person's head The occipital anchor 120, the forward anchor 180 and the biasing structure 240 are substantially aligned along the axis A of symmetry of the person's head, which is in line with the plane of FIG. 14.

The biasing structure 240 extends between the occipital anchor 120 and the forward anchor 180 a distance within the range of about 7-30 centimeters, preferably about 10-18 centimeters. The biasing structure 240 can be formed of spring steel, and as shown in FIG. 11, the distance between the occipital anchor 120 and the forward anchor 180 can be adjusted by spring 260 sliding within slot 280 of scabbard member 300.

Referring to FIG. 11, a mounting member 320 is connected to the biasing structure 240 for mounting a breathing mask 340, which in this case is a nostril mask 340A, to sealingly engage the nostril mask with a person's nostrils.

The mounting member 320 can extend between the forward anchor 180 and the breathing mask 340 a distance within the range of about 10 to 25 centimeters, preferably about 15 to 20 centimeters. As shown in FIG. 11, the device 100 has a second scabbard member 360 with a slot 380 within which the spring member 260 is slidable for adjustment of the device.

Figure 12:
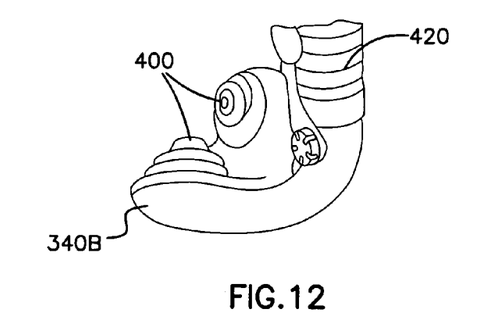
FIG. 12 shows details of a mask for use with the CPAP device of FIG. 11 including a pair of nostril-tubes for sealingly fitting within corresponding nostrils of a person's nose.

FIG. 12 shows a breathing mask 340B which is a Nasal Pillows™ type including a pair of nostril-tubes 400 for sealingly fitting within corresponding nostrils of a person's nose.

FIG. 13 shows a breathing mask 340C which sealingly covers both the patient's nose and mouth, the mounting member 320 being capable of biasing the breathing mask 340C so as to form a seal around the nose and mouth orifices.

In the embodiments shown, a gas plenum 420 is provided, as shown in FIGS. 12, 13 and 14. The embodiment shown in FIG. 11 shows structure for attaching a gas plenum to mounting member 320, including rings 440. The gas plenum is attached to the mounting member 320 and connectable to the breathing mask 340 for delivering gas to and from the breathing mask 340. Alternatively, the gas plenum can be formed as an integral part of mounting member 320.

The plenum 420 can have any suitable cross-sectional area, for example, within a range of about 100 to 500 mm$^2$. In particularly preferred embodiments, the air plenum 420 is approximately 460 centimeters long and has a circular cross-section of 15 mm, with a cross-sectional area of about 175 mm$^2$.

For increased security and/or to provide greater fixation of the device, a side strap 480 can be provided as shown in FIG. 14, passing around the sides of the head and connecting the occipital anchor 120 with the mounting member 320. Side strap 480 preferably is formed of cloth or elastomeric material.

In the embodiment shown in FIG. 11, carbon dioxide-rich gas that the patient exhaled exits the system through vent 460 which is sized so that continuous positive airway pressure (CPAP) within the plenum flushes the hose and the plenum between breaths. A carbon dioxide vent is generally disclosed in U.S. Pat. No. 5,065,756, reissued as RE. 35,339, incorporated herein by reference.

E. Coordinated Positive Airway Pressure and Palate Treatment

At higher pressures, pressure-related side effects are more likely to occur. These include dryness of mouth and throat. Further, at higher pressures a patient may find it more difficult to breath. Also, if a patient is using a long air hose from the pressure machine to mask (e.g., to increase the distance to the pressure machine to reduce the sleep disruption from any noise of the machine), the pressure drop of the longer hose may make it difficult to achieve a higher pressure. All of these can lead to a decrease in patient compliance with a positive airway pressure machine.

A patient's tolerance to positive airway pressure will vary from patient to patient. An individual patient will have a threshold pressure above which the patient's likelihood of compliance with CPAP will drop off. For example, patients frequently have difficulty tolerating a CPAP titrated above a pressure of about 11 cm $H_2O$. At such pressures, compliance is estimated at about 30%. For low pressures (about 4 cm $H_2O$), compliance is estimated to be much higher (about 90%). At higher pressures (e.g., about 20 cm $H_2O$), compliance rates are estimated to be as low as 10%. It will be appreciated these estimates are aggregates for the patient population. An individual's pressure threshold leading to low compliance will vary from patient to patient.

FIG. 17 illustrates these estimates in graphical form to show the relation between patient compliance with a PAP therapy and PAP operating pressures. The horizontal axis is the operating pressure of a PAP. The vertical axis the estimate of a patient population's compliance with the PAP therapy. The line f(x) is the plot of the population's compliance as a function of pressure. Representative points on this function curve are shown for operating pressures of 4, 11 and 20 cm $H_2O$ operating pressures. At the low pressure (4 cm $H_2O$), compliance is estimated to be 90%. At the high pressure (20 cm $H_2O$), compliance is estimated at 10%. At 11 cm $H_2O$, patient compliance is estimated at 30%.

As shown as line A, a hypothetical patient not otherwise treated may have a titrated operating pressure of 13 cm $H_2O$. This patient is estimated as having of about 20% compliance. While the patient may not be a candidate for palatal stiffening since the patient's AHI is too great (e.g., the patient may not be categorized as mild to moderate OSA), a palatal stiffening procedure will lower the patient's titrated PAP level below the original threshold level. Line B illustrates a 4 cm $H_2O$ decrease in the patient's pressure titration as a consequence of the palatal stiffening procedure. Line C illustrates an 8 cm $H_2O$ decrease. The amount of decrease will vary from patient to patient. For example a s reduction as high as 11 cm $H_2O$ is reasonable expectation (see, e.g., Seemann, et al., supra). From line A to line B, the patient's likely compliance rate has improved from about than 20% to about 50%. From line A to line C, the improvement is to almost 90%. Since the pressure threshold tolerance varies from individual to individual, even a small decrease in PAP titration pressure can markedly improve the patient's compliance. As a result, for a large number of patients, palatal stiffening, while not necessarily curing the particular patient's OSA, can significantly lower the titratable PAP pressure below the patient's tolerance threshold thereby increasing the patient's compliance with the PAP therapy and increasing the likelihood the patient will enjoy the health benefits of therapy compliance.

The combination of palatal stiffening with PAP increases the likelihood of patient compliance with PAP and increases the likelihood of patient's suffering from severe OSA being effectively treated for this serious disease. Also, the combination therapy provides opportunities for cooperative treatments involving different professionals. For example, sleep studies, PAP titration and PAP therapies are often prescribed by pulmonologists. A different medical specialty (commonly, otolaryngologists) perform palatal stiffening procedures as described herein. With a cooperative treatment, a pulmonologist can prescribe and monitor a PAP compliance. If compliance is unsatisfactory (and even if the patient has severe OSA), the pulmonologist can refer the patient to an otolaryngologist for palatal stiffening with the patient returned back to the pulmonologist for continued PAP therapy at an anticipated higher rate of compliance.

The present invention has been described in a first preferred embodiment for treating a patient with obstructive sleep apnea with a combination of palatal stiffening and positive airway pressure. In a preferred embodiment, the palatal stiffening is achieved by delivery of a braided implant into tissue of the soft palate. It will be appreciated the present invention covers a wide variety of palatal stiffening techniques including other implant designs (e.g., instead of the braided implant, the implant may be a bolus of particulate material as described in U.S. Pat. No. 6,431,174 or a sheet of fibrosis-inducing material as described in U.S. Pat. No. 6,523,542), injected stiffening agents (e.g., sclerosing therapies such as those described in Brietzke et al., "Injection Snoreplasty: How to Treat Snoring Without All the Pain and Expense", *Otolaryngology-Head and Neck Surgery*, Vol. 124, No. 5, pp. 503-510 (May 2001)) or collagen injections (DE 44 12 190 A1 published Oct. 12, 1995) or ablation techniques (such as radio-frequency ablation as described in Blumen, et al., "Radiofrequency Ablation for the Treatment of Mild to Moderate Obstructive Sleep Apnea", *Laryngoscone*, pp. 2086-2092 (2002)). Other stiffening techniques include magnet stiffening (such as those shown in U.S. Pat. No. 4,978,323 to Freeman or U.S. patent application Publication No. 2004/0139975 A1 published Jul. 22, 2004 (both incorporated herein by reference) and electrical stimulation (such as described in commonly assigned U.S. Pat. No. 6,636,767 issued Oct. 21, 2003). Further, while palatal tissue is described as the preferred airway tissue for stiffening in combination with PAP, other airway tissue may be stiffened (e.g., nasal, tongue or pharyngeal wall). Further, the airway pressure treatment may be conventional positive airway pressure, variable positive airway pressure (as described in U.S. Pat. No. 6,752,151 incorporated herein by reference) or a bi-level pressure support device or other airway pressure support for obstructive sleep apnea treatment.

What is claimed is:

1. A method for treating a patient diagnosed with obstructive sleep apnea, said method comprising:
   identifying a patient as having sleep apnea susceptible to a first positive airway treatment at a first pressure level sufficiently high to contribute to an unsatisfactory patient compliance with said first airway treatment;
   said first positive airway treatment including generating an air flow at said first pressure and admitting said first air flow into said patient's airway with said first pressure estimated to be sufficient to treat said apnea;
   treating said patient with an airway treatment selected to alter a portion of an airway tissue of said patient;
   said airway treatment consisting essentially of placement of a member completely embedded within said airway tissue and selected to alter a stiffness of said airway tissue to an increased stiffness sufficient to increase a resistance of said tissue to deformation and with said airway treatment alone insufficient to fully treat said apnea;
   treating said patient with a second positive airway treatment while said member is embedded within said airway tissue and with said second positive airway treatment at a second pressure lower than said first pressure and selected to contribute to an enhanced patient compliance relative to said first airway treatment;
   said second positive airway treatment including generating an air flow at said second pressure, and admitting said second air flow into said patient's airway with said second positive airway treatment in combination with said altered stiffness treating said apnea; and
   retaining said member embedded within said tissue following discontinuance of said second positive airway treatment.

2. A method according to claim 1 wherein said airway tissue is a palatal tissue of said patient.

3. A method according to claim 1 wherein said airway tissue is a nasal tissue of said patient.

4. A method according to claim 1 wherein said airway tissue is a tongue tissue of said patient.

5. A method according to claim 1 wherein said airway tissue is a pharyngeal wall tissue of said patient.

6. A method according to claim 1 wherein said airway treatment includes placement of a fibrosis-inducing member in said tissue with said fibrosis-inducing member selected to induce formation of fibrosis in said airway tissue following said placement.

7. A method according to claim 1 wherein said airway treatment includes placement of a stiffening member in said tissue with said stiffening member having a material stiffness selected to increase a stiffness of said airway tissue following said placement.

8. A method according to claim 1 wherein said airway treatment includes placement of a magnetic field-responsive material in said tissue with said magnetic field-responsive material selected to urge said airway tissue to maintain a patency of an airway of said patient in response to a cooperating magnetic field.

9. A method according to claim 1 wherein said second pressure is at least 11 cm $H_2O$ lower than said first pressure.

* * * * *